United States Patent [19]
Welch et al.

[11] Patent Number: 5,442,116
[45] Date of Patent: Aug. 15, 1995

[54] PROCESS FOR PREPARING SERTRALINE INTERMEDIATES

[75] Inventors: Willard M. Welch, New London, Conn.; Michael T. Williams, Deal, United Kingdom

[73] Assignee: Pfizer Inc., New York, N.Y.

[21] Appl. No.: 178,240

[22] PCT Filed: Jul. 3, 1992

[86] PCT No.: PCT/EP92/01496
§ 371 Date: Jan. 10, 1994
§ 102(e) Date: Jan. 10, 1994

[87] PCT Pub. No.: WO93/01161
PCT Pub. Date: Jan. 21, 1993

[30] Foreign Application Priority Data
Jul. 11, 1991 [GB] United Kingdom ............ 9114948

[51] Int. Cl.⁶ ............ C07C 233/03; C07C 233/04; C07C 231/18
[52] U.S. Cl. ............ 564/222; 564/215; 564/217; 564/218; 564/219
[58] Field of Search ............ 564/275, 217, 218, 219, 564/222; 514/625, 629, 639

[56] References Cited
U.S. PATENT DOCUMENTS
4,536,518 8/1985 Welch, Jr. et al. ............ 514/647

OTHER PUBLICATIONS
Tremaine ete al., Drug Metabol. Dispos., 17(5) 1989 542–550.
Welch et al. J. Med. Chem., 1984, 27, 1508–1515.

*Primary Examiner*—Shailendra Kumar
*Attorney, Agent, or Firm*—Peter C. Richardson; Paul H. Ginsburg

[57] ABSTRACT

The invention provides the substantially geometrically and optically pure trans-stereoisomeric form of a compound of formula (I):

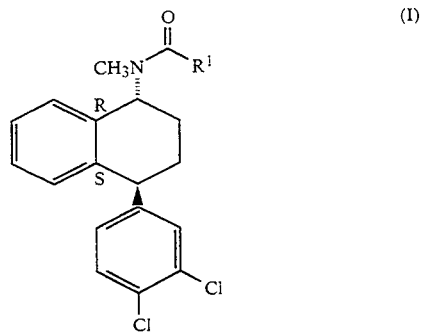

wherein $R^1$ is H or $C_1$–$C_4$ alkyl, together with processes for its preparation. The compounds are intermediates for the preparation of the antidepressant agent known as sertraline.

12 Claims, No Drawings

PROCESS FOR PREPARING SERTRALINE INTERMEDIATES

BACKGROUND OF THE INVENTION

This application is a 371 of PCT/EP92/01496 filed Jul. 3, 1992.

This invention relates to novel trans-N-alkanoyl-N-methyl-4-(3,4-dichlorophenyl) -1,2,3,4-tetrahydro-1-naphthylamine analogues, which are intermediates in a new process for preparing sertraline, together with intermediates thereto and processes for the preparation thereof.

SUMMARY OF THE INVENTION

More specifically, the invention relates to the (1R,4S)-stereoisomeric form of the said trans-1,4-disubstituted tetrahydronaphthylamines which, upon N-deacylation, afford trans-(1R,4S)-N-methyl-4-(3,4-dichlorophenyl)-1,2,3,4-tetrahydro-1-naphthylamine. The latter, which is disclosed in U.S. Pat. No. 4,556,676 and in the Journal of Medicinal Chemistry, 1984, 27, 1508, is isomeric with the antidepressant agent known as sertraline, or cis-(1S,4S)-N-methyl-4-(3,4-dichlorophenyl)-1,2,3,4-tetrahydro-1-naphthylamine, which, in turn, is disclosed in U.S. Pat. No. 4,536,518 and in the Journal of Medicinal Chemistry, 1984, 27, 1508. The trans-(1R,4S)-isomer may be converted to the cis-(1S,4S)-isomer (sertraline) by the conventional procedures subsequently summarised.

The novel compounds of the present invention have been made available by the unexpected discovery that the required trans-isomer may be generated stereoselectively, in high yield, by ionic hydrogenation of the appropriate (1R, 4S)-N-alkanoyl-N-methyl-4-(3,4-dichlorophenyl)-4-hydroxy-1,2,3,4-tetrahydro-1-naphthylamine precursor, allowing ready removal of the unwanted (1R,4R)-isomer. Importantly, since the said precursor possesses the 1-(N-alkanoyl)methylamino substituent in the R-configuration, ionic hydrogenation thereof affords the trans-(1R,4S)-enantiomer in high yield and with high stereoselectivity, thus obviating the need for a subsequent optical resolution to remove the unwanted trans-(1S,4R)-enantiomer.

Thus the present invention provides:
a) the substantially geometrically and optically pure trans-stereoisomeric form, consisting of the trans-(1R,4S)-enantiomer, of a compound of formula:

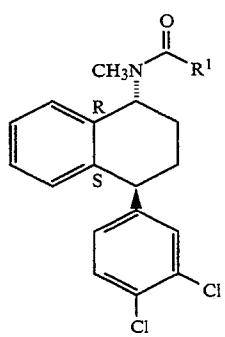

(I)

wherein $R^1$ is H or $C_1$–$C_4$ alkyl, and R and S represent the absolute configurations of the asymmetric centres;

b) a process for preparing the substantially geometrically and optically pure trans-stereoisomeric form of a compound of formula (I) by subjecting a compound of formula:

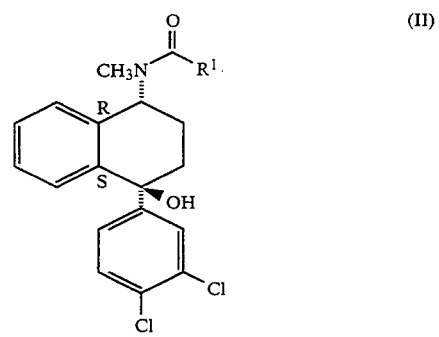

(II)

wherein $R^1$, R and S are as previously defined for formula (I), in a suitable solvent, to ionic hydrogenation conditions.

Alkyl groups containing three or four carbon atoms may be straight or branched chain.

The term "substantially geometrically and optically pure" means that the compound of the formula (I) contain less than 4%, and preferably less than 2%, of the undesired cis-(1R,4R)-enantiomer.

In the above definitions of the compounds of formulae (I) and (II), preferably $R^1$ is H.

DETAILED DESCRIPTION OF THE INVENTION

The compounds provided by the present invention may be prepared as follows.

A compound of formula (I) is obtained by ionic hydrogenation of a compound of formula (II) in a suitable solvent, such as dichloromethane, using a combination of either a protic acid, e.g. trifluoroacetic acid, or preferably a Lewis acid, e.g. boron trifluoride, with a hydride donor, e.g. triethylsilane. Typically the reaction is conducted at from −40° to +25° C. for up to to 40 hours, preferably about 20 hours. The product of formula (I) may then be isolated and purified by conventional techniques, e.g. by extractive work-up, followed by chromatographic purification and/or crystallisation of the crude product, to remove any recovered starting material and minor amounts of the unwanted cis-(1R,4R)-isomer. Alternatively, the separation of trans- and cis-isomers can be effected after removal of the N-alkanoyl group, to furnish a compound of formula (VI), wherein R and S are as previously defined, in the next stage of the synthetic sequence depicted in the following Scheme.

Scheme

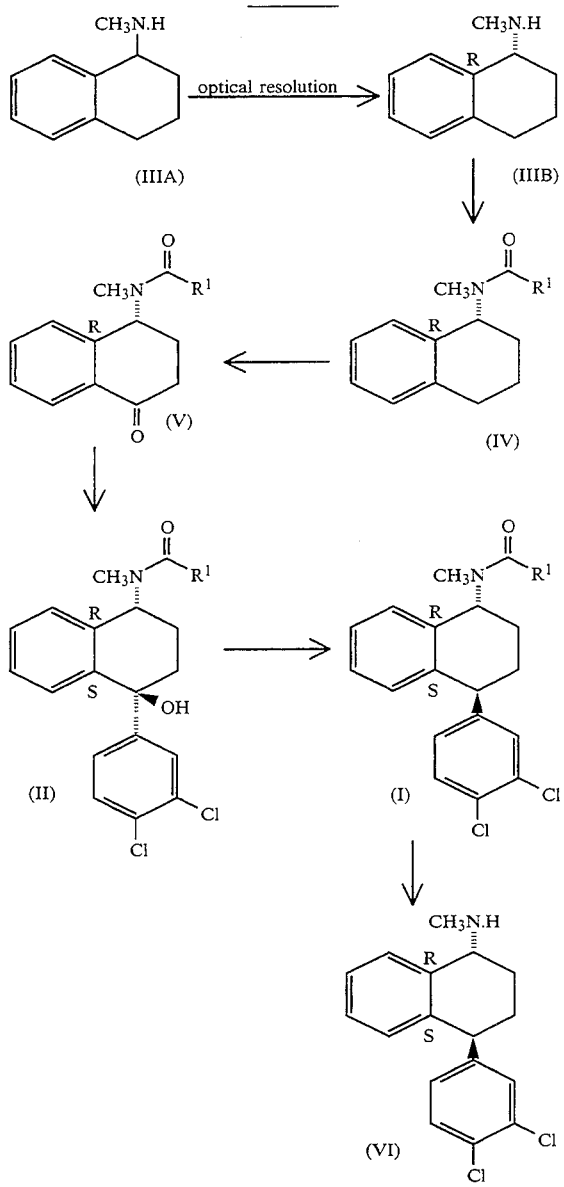

The N-alkanoyl group of a compound of formula (I), the major isomer of the aforementioned crude product, is removed by hydrolysis, using an aqueous inorganic base such as an alkali metal hydroxide salt, preferably potassium hydroxide, as a 10 molar solution in water. Typically the hydrolysis is carried out in ethylene glycol at the reflux temperature of the reaction medium for from 2 hours to 4 days. For a compound of formula (I) wherein $R^1$ is H, the N-alkanoyl group is preferably removed by acidic hydrolysis using a mineral acid, e.g. hydrochloric acid, in a suitable solvent such as 2-propanol, 1,4-dioxan or ethyl acetate, at the reflux temperature of the reaction medium for from 2 to 8 hours. The product (VI) is then isolated and purified by conventional procedures, e.g. extractive work-up, optional coltram chromatography to remove minor amounts of the unwanted cis-(1R,4R)-isomer, and conversion to the hydrochloride salt. The purified free amine may then be transformed to the cis-(1S,4S)-enantiomer (sertraline), as summarised on page 9 et seq.

A compound of formula (II) required for the preparation of a compound of formula (I) may be obtained by the route depicted in the Scheme, wherein $R^1$, R and S are as previously defined, using routine procedures.

Initially, resolution of the amine (IIIA) is effected to provide the optically pure R-enantiomer (IIIB). The resolution is carried out in a conventional manner by fractional crystallisation of a salt of the amine (IIIA), formed with an optically pure acid such as a sulphonic or carboxylic acid, preferably (2R,3R) (+) tartaric acid, from an appropriate solvent, e.g. water. The free amine (IIIB) is then liberated by treatment of the resolved amine salt with a base, typically an aqueous solution of sodium or potassium hydroxide.

The amine (IIIB) may also be obtained by asymmetric reduction of the imine precursor, which is directly accessible from α-tetralone and methylamine, by methods well known to persons skilled in the art.

A compound of formula (IV) wherein $R^1$ is $C_1$–$C_4$ alkyl can be prepared by acylating a compound of the formula (IIIB) with either an acyl halide of formula (C₁-C₄alkyl)CO(Cl or Br) or with an acid anhydride of formula [(C₁-C₄ alkyl)CO]₂O. When an acyl halide is employed the reaction may be carried out at from 0° to 25° C., preferably at from 5° to 10° C., in a suitable organic solvent, e.g. dichloromethane, and in the presence of an acid acceptor, e.g. triethylamine. When an acid anhydride is used the reaction may be conducted at up to the reflux temperature of the reaction medium, preferably at 100° C., in a suitably compatible solvent, e.g. a carboxylic acid of formula (C₁-C₄ alkyl)CO₂H. To obtain a compound of formula (IV) wherein R¹ is H, compound (IIIB) is formylated using acetic-formic anhydride which may be generated by the addition of 98% formic acid to stirred acetic anhydride, typically between 0° and 10° C. The freshly prepared mixed anhydride is then reacted with compound (IIIB) in an appropriate solvent, e.g. 98% formic acid, at from 5° to 25° C.

Conversion of a compound of formula (IV) to a ketone of formula (V), via a benzylic oxidation reaction, can be effected with a variety of oxidising agents such as an inorganic permanganate salt, ammonium cerium(F) nitrate, cobalt(III) acetate or 2,3-dichloro-5,6-dicyano-1,4-benzoquinone, in a suitable solvent. Preferably the reaction is carried out using 3-5 molecular equivalents of potassium permanganate in aqueous acetone in the presence of a buffering reagent such as an alkali, or alkaline earth, metal salt, e.g. magnesium sulphate. The oxidant may be added in portions in a controlled manner, in order to moderate the potentially vigorous reaction, to a solution of the substrate (IV) at from 5° to 30° C. Subsequent to this addition, warming of the reaction mixture at from 30° to 50° C. may be required in order to complete the oxidation.

A compound of formula (II) can be prepared stereoselectively from a compound of formula (V) using a 3,4-dichlorophenylmagnesium halide, preferably the iodide, under standard Grignard reaction conditions. Thus, typically, a solution of the ketonic substrate (V) in a suitably compatible solvent, e.g. dry toluene or dry tetrahydrofuran, is added to a freshly prepared solution of the Grignard reagent in an appropriate solvent such as dry diethyl ether, at a temperature of from 5° to 25° C., under anhydrous conditions. The reaction is allowed to proceed at from 20°-25° C. for from 4 to 24 hours and the mixture may be heated under reflux for up to 1 hour, if necessary, to promote a better conversion of (V) to (II). Minor amounts of the (1R,4R)-alcohol may be removed by column chromatography and/or crystallisation. The trans-(1R,4S)-amine (VI) may be converted to sertraline by the following Process.

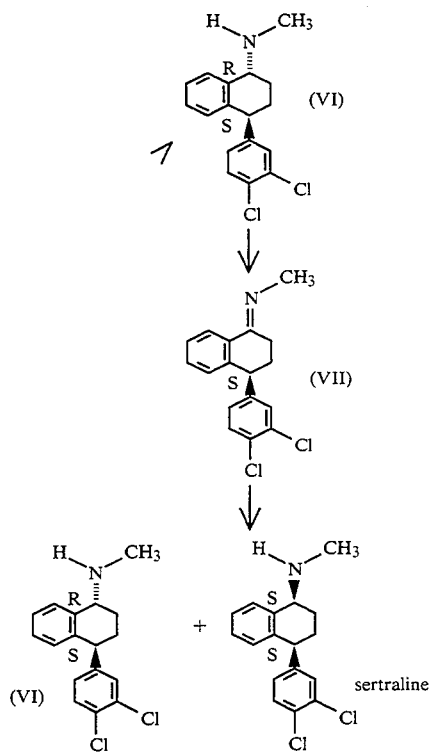

The process involves controlled oxidation of the trans-enantiomer (VI) to afford the imine (VII) which is subsequently reduced, for example by catalytic hydrogenation using 10% palladium on charcoal as catalyst as described in U.S. Pat. No. 4,536,518, to provide a mixture (approximately 7:3 ratio) of sertraline and regenerated (VI); the latter can be separated from sertraline by conventional means and recycled to provide further batches of sertraline. Alternatively, nickel based catalysts may be used in the hydrogenation step to afford a mixture (approximately 8:1 ratio) of sertraline and (VI).

In an alternative process optimisation procedure illustrated below, the cis-(1R,4R)-enantiomer (VIII), which in common with (VI) is an unwanted by-product of processes in which sertraline is produced by resolution of a mixture of all four stereoisomers, may also be recycled to sertraline via the imine (VII). Firstly, however, (VIII) is isomerised by base treatment to a mixture (approximately 2:1 ratio) of (VIII) and the trans-(1R,4S)-enantiomer (VI); the latter is then separated, and converted to imine (VII) as in the first recycle process disclosed above. Clearly, the remaining cis-(1R,4R)-enantiomer (VIII) can re-enter this base equilibration process as required.

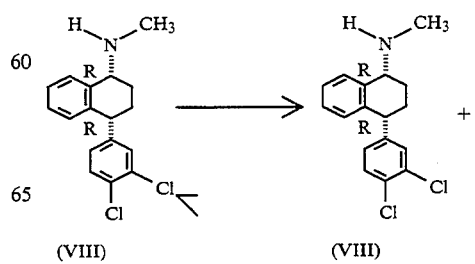

-continued tetralone (X), disclosed in U.S. Pat. No. 4,536,518 and the Journal of Medicinal Chemistry, 1984, 27, 1508. (X) is then transformed to sertraline via racemic imine (XI), preferably by catalytic hydrogenation of (XI) using a palladium or nickel catalyst as mentioned above, followed by separation of the cis-racemate and its subsequent resolution as described in U.S. Pat. No. 4,536,518. This process is depicted overleaf.

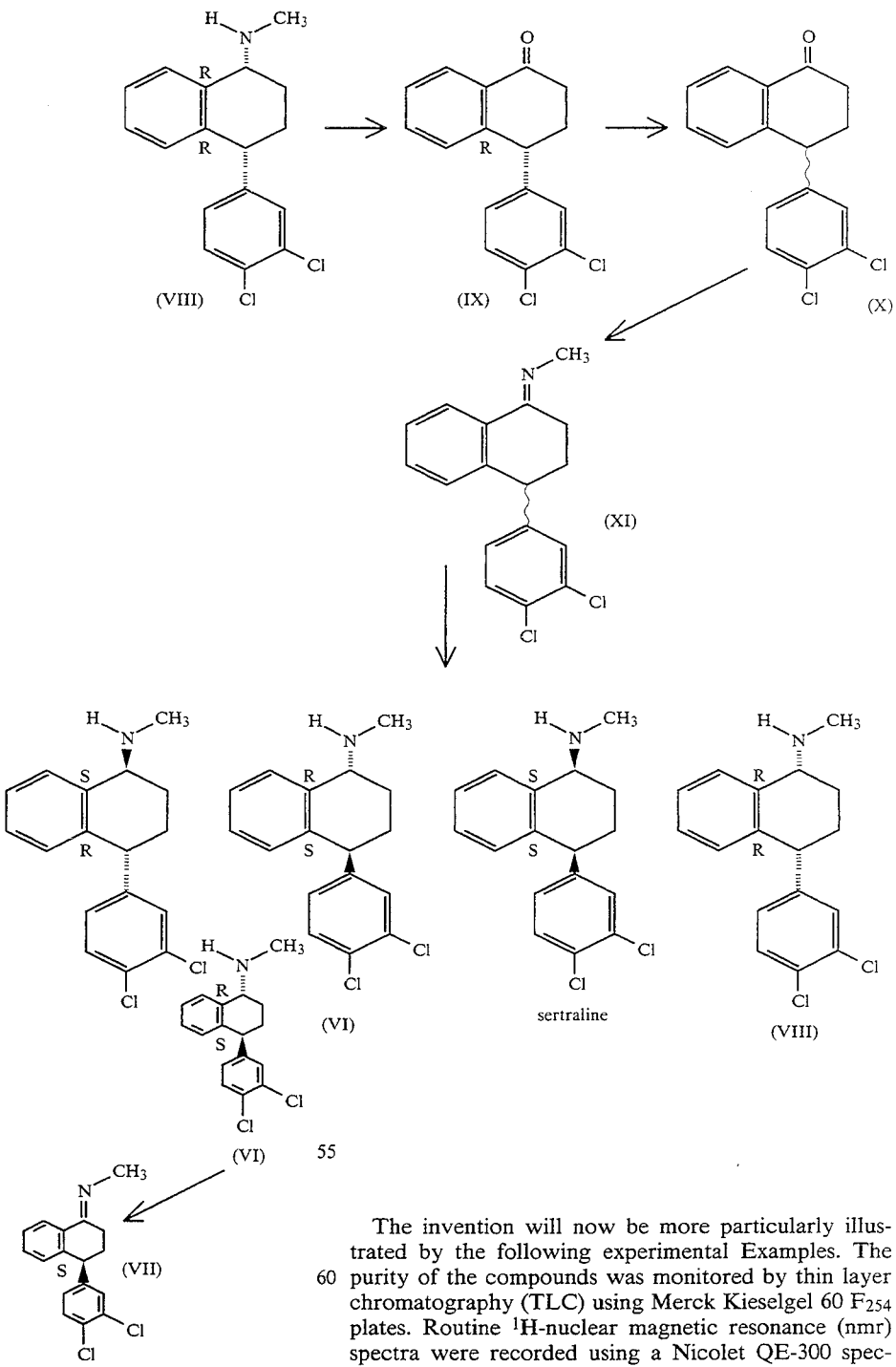

Alternatively, in a related process, the unwanted cis-(1R,4R)-enantiomer (VIII) may be oxidised to the α-tetralone (IX) which, in turn, can be isomerised to furnish the known, racemic 4-(3,4-dichlorophenyl)-α-

The invention will now be more particularly illustrated by the following experimental Examples. The purity of the compounds was monitored by thin layer chromatography (TLC) using Merck Kieselgel 60 $F_{254}$ plates. Routine $^1$H-nuclear magnetic resonance (nmr) spectra were recorded using a Nicolet QE-300 spectrometer and $^{13}$C nmr spectra were recorded using a Bruker 250 spectrometer; they were in all cases consistent with the proposed structures. Nuclear Overhauser effect (nOe) experiments were conducted using a Bruker 250 spectrometer.

EXAMPLE 1

(R) (-)-N-Methyl-1,2,3,4-tetrahydro-1-naphthylamine

A solution of (2R,3R) (+) tartaric acid (160.3 g) in water (500 ml) was treated with N-methyl-1,2,3,4-tetrahydro-1-naphthylamine (172.2 g). The resulting solution was cooled from 33° C. to room temperature, seeded and stirred for 16 hours. The slurry was refrigerated for 4 hours, filtered and the solid was washed with water (3×50 ml). The crude salt (196.2 g) was fractionally recrystallised from water giving the purified (+) tartaric acid salt of the title compound (42 g, 25.3% based on available enantiomer) as white crystals, m.p. 107°–109° C., $[\alpha]_D + 12.3°$ (c=4.2, water). Found C,54.85; H,7.06; N,4.22. $C_{15}H_{21}NO_6$; $H_2O$ requires C,54.70; H,7.04; N,4.25%.

The salt (38.9 g) was dissolved in water (150 ml), with warming to 40° C., and then basified by the addition of 5N aqueous sodium hydroxide solution (100 ml). The cooled mixture was extracted with dichloromethane (2×150 ml). Evaporation under vacuum of the extracts gave the title compound as a colourless oil (19.1 g, 97.2% from salt), $[\alpha]_D - 10.3°$ (c=5, EtOH). $^1$H-nmr assay of the (+)-α-methoxy-α-(trifluoromethyl)-phenylacetyl derivative using the method of Mosher (J. Org. Chem., 1969 34, 2543) showed the title compound to be a 95.5:4.5 mixture of the (R) and (S) enantiomers, respectively.

EXAMPLE 2

(R)(+)-N-(1,2,3,4-Tetrahydro-1-naphthyl)-N-methylformamide

Acetic anhydride (54.1 g) was chilled to 0° C. and stirred as 98% formic acid (33.1 g) was added over 30 minutes, keeping the temperature below 5° C. The solution was warmed to 50° C., held at this temperature for 15 minutes, and chilled to 5° C. The resulting solution of acetic-formic anhydride was added over 5 minutes to a stirred, chilled solution of (R)(−)-N-methyl-1,2,3,4-tetrahydro-1-naphthylamine (19.08 g) in 98% formic acid (19.08 ml), keeping the temperature below 10° C. The reaction solution was warmed to room temperature, stirred for 1 hour, poured into an ice-water mixture (200 g) and stirred for 30 minutes. The mixture was basified to pH 9 with 10N aqueous sodium hydroxide solution (about 230 ml) and extracted with dichloromethane (3×200 ml). The combined extracts were back-washed with 1N aqueous hydrochloric acid (100 ml), then water (100 ml), and evaporated under vacuum to give the title compound (21.63 g, 96.6%) as a solid, m.p. 53°–55° C.; Rf 0.80 (silica; chloroform, methanol; 95:5).

A sample of the product (1.5 g) was crystallised from a mixture of ethyl acetate (1.5 ml) and hexane (15 ml) to give a purified sample of the title compound (0.92 g, 61.3% recovery) as white crystals, m.p. 55°–56° C., $[\alpha]_D + 19.4°$ (c=0.5, EtOH). A chiral HPLC assay on an acetylated β-cyclodextrin column showed this material to contain less than 1% of the (S)-enantiomer. Found: C,76.04; H,7.94; N,7.43. $C_{12}H_{15}NO$ requires C,76.16; H,7.98; N, 7.40%.

$^1$H-nmr (300 MHz, CDCl$_3$): δ=1.80–2.13 (m,4H), 2.70 and 2.73 (2 NMe rotamer singlets, 3H), 2.78–2.93 (m,2H), 4.73–4.81 and 5.71–5.79 (2 rotamer multiplets, 1H), 7.02–7.25 (m, 4H), 8.30 and 8.34 (2 formyl CH rotamer singlets, 1H) p.p.m.

EXAMPLE 3

(R) (+)-N-(1,2,3,4-Tetrahydro-4-keto-1-naphthyl)-N-methylformamide

To a chilled solution of (R)(+)-N-(1,2,3,4-tetrahydro-1-naphthyl)-N-methylformamide (19.1 g) in acetone (430 ml) was added magnesium sulphate heptahydrate (57 g), water (143 ml) and then, portionwise over 1 hour, potassium permanganate (76 g). The mixture was stirred for 5.5 hours with water bath cooling to keep the reaction temperature below 34° C., filtered and the cake washed with acetone (2×100 ml). The filtrate and washes were combined and treated with 10% aqueous sodium metabisulphate solution (140 ml), then the mixture refiltered and extracted with dichloromethane (400 ml and then 200 ml). The combined extracts were evaporated under vacuum to an oil (14.7 g) which was chromatographed on silica (274 g), eluting with a dichloromethane/methanol mixture (98:2) to give the product as an oil (8.2 g, 40%); Rf 0.18 (silica; ethyl acetate) and 0.58 (silica; chloroform, methanol; 95:5).

A sample of the product (1.1 g) was triturated with diethyl ether (20 ml) to induce crystallisation giving a purified sample of the title compound (0.72 g) m.p. 92°–93° C.; $[\alpha]_D + 54$ 9° (c=0.5, EtOH). Found: C,70.68; H,6.41; N,6.86. $C_{12}H_{13}NO_2$ requires C,70.92; H,6.45; N,6.64%.

$^1$-nmr (300 MHz, CDCl$_3$]: δ=2.17–2.56 (m, 2H), 2.68–2.99 (m,2H), 2.79 and 2.83 (2 NMe rotamer singlets, 3H), 4.96–5.04 and 5.92–6.01 (2 rotamer quartets, 1H), 7.10–7.24 (q, 1H), 7.40–7.53 (m, 1H), 7.55–7.68 (m, 1H), 8.07–8.16 (t, 1H), 8.38 and 8.40 (2 formyl CH rotamer singlets, 1H) p.p.m.

EXAMPLE 4

(1R,4S)(−)-N-[4-(3,4-Dichlorophenyl)-1,2,3,4-tetrahydro-4-hydroxy-1-naphthyl-N-methylformamide Magnesium turnings (0.89 g) and a crystal of iodine were stirred in dry diethyl ether (25 ml) as a solution of 1,2-dichloro-4-iodobenzene (10.07 g) in dry diethyl ether (25 ml) was added over 20 minutes. After the exotherm subsided the mixture was heated under reflux for a further 25 minutes to complete the consumption of the magnesium metal. The mixture was then chilled to 5° C., blanketed with nitrogen gas and a solution of (R)(+)-N-(1,2,3,4-tetrahydro-4-keto-1-naphthyl)-N-methylformamide (5 g) in dry toluene (100 ml) was added over 15 minutes. After being stirred for 20 hours the resulting mixture was poured into 10% aqueous ammonium chloride solution (200 ml). The phases were separated, the aqueous layer was washed with toluene (25 ml) and the combined organic layers were evaporated under vacuum to give a mixture of (1R,4S)- and (1R,4R)-isomers (ratio 87:13 respectively by nmr spectroscopy techniques) as a dark oil (10.17 g) which was chromatographed on silica (320 g). Elution with hexane-ethyl acetate mixtures (1:1 to 1:4) gave the title compound as a foam (3.94 g, 45.7%), Rf 0.34 (silica; ethyl acetate) and 0.50 (silica; chloroform, methanol; 95:5) which was sufficiently pure for use in the next step.

A sample of the product (0.92 g) was purified by slow crystallisation from di-2-propyl ether giving the title compound (0.46 g, 50% recovery) as white crystals, m.p. 123°–125° C., $[\alpha]_D - 31.6°$ (c=0.5, EtOH). Found:

C,61.79; H,5.07; N,3.90. C₁₈H₁₇Cl₂NO2 requires C,61.72; H,4.89; N,4.00%.

¹H-nmr (300 MHz, CDCl₃): δ=1.60-2.01 (m,2H), 2.12-2.37 (m, 2H), 2.38 (s, 1H), 2.69 and 2.73 (2 NMe rotamer singlets, 3H), 4.78-4.86 and 5.75-5.83 (2 rotamer quartets, 1H), 6.89-7.04 (m, 1H), 7.05-7.42 (m, 6H), 8.25 and 8.30 (2 formyl CH rotamer singlets, 1H) p.p.m.

EXAMPLE 5 trans-(1R,4S)(+)-N-[4-(3,4-dichlorophenyl)-1,2,3,4-tetrahydro-1-naphthyl]-N-methyl formamide To a solution of (1R,4S) (+)-N-[4-(3,4-dichlorophenyl)-1,2,3,4-tetrahydro-4-hydroxy-1-naphthyl]-N-methylformamide (0.175 g) in dichloromethane (10 ml) was added triethylsilane (0.13 g) in dichloromethane (1 ml). The resulting solution was cooled to −40° C. and stirred as boron trifluoride (0.08 g) in dichloromethane (6.5 ml) was added over 30 minutes. The solution was allowed to warm to room temperature over 90 minutes and then treated with further triethylsilane (0.13 g) in dichloromethane (1 ml) followed by further boron trifluoride (0.54 g) in dichloromethane (43.5 g). After overnight stirring at room temperature a third addition of triethylsilane (0.13 g) was made and the solution was gassed with boron trifluoride for about 1 minute. The resulting solution was washed with 2M aqueous sodium carbonate solution (22 ml) and then saturated brine (25 ml), and the aqueous phases were combined and backwashed with diethyl ether (2×25 ml). The combined organic extracts were dried over magnesium sulphate and evaporated under vacuum to give an oil (0.17 g) which was percolated through a column of silica (16 g) eluting with 1:1 ethyl acetate-hexane to remove the low level of recovered starting material. Evaporation under vacuum of the requisite fractions gave the crude product as an oil (154 mg, 92%). A ¹H-nmr assay of this material showed it to be an 86:14 mixture of the required (1R,4S) trans-isomer (δ=4.04-4.14 p.p.m., m, for the H₄ proton) and the (1R,4R) cis-isomer (δ=4.18-4.27 p.p.m., m, for the H₄ proton), respectively.

The separation of trans and cis-isomers is most efficiently achieved after removal of the formyl group. However, crystallisation of a sample of the crude product from 1:3 dichloromethane-hexane provided a reference sample of the title Compound as white crystals, m.p. 110°-112° C.; Rf 0.62 (silica; chloroform, methanol; 95:5); [α]_D+100.8° (c=1.03, EtOH). Found: C,64.66; H,5.37; N,4.12. C₁₈H₁₇Cl₂NO requires C,64.67; H,5.13; N, 4.19%.

¹H-nmr (300 MHz, CDCl₃): δ=1.88-2.18 (m, 3H), 2.21-2.37 (m, 1H), 2.73 and 2.78 (2 NMe rotamer singlets, 3H), 4.04-4.14 (m, 1H), 4.90-4.98 and 5.84-5.96 (2 rotamer multiplets, 1H), 6.77-6.85 (t, 1H), 6.91-7.03 (m, 1H), 7.05-7.34 (m, 4H), 7.36-7.47 (m, 1H), 8.34 and 8.38 (2 formyl CH rotamer singlets, 1H) p.p.m.

EXAMPLE 6 trans-(1R,4S)(+)-N-Methyl-4-(3,4-dichlorophenyl)-1,2,3,4-tetrahydro-1-naphthylamine hydrochloride A solution of trans-(1R,4S)(+)-N-[4-(3,4-dichlorophenyl)-1,-2,3,4-tetrahydro-1-naphthyl]-N-methylformamide (0.15g of 86:14 trans-cis mixture from Example 5) in 2-propanol-(1.5ml) was treated with concentrated aqueous hydrochloric acid (0.45 ml) and heated under reflux for 12.5 hours. The solution was refrigerated overnight, then the resulting mixture granulated at 0° C. for several hours. Filtration gave the product (0.110g, 71.4%) as white crystals, m.p. 253°-255° C.; Rf 0.09 (silica; chloroform, methanol; 90:10); [α]_D+41.4° (c=1, MeOH).

N.B. N-Methyl-1,2,3,4-tetrahydro-1-naphthylamine (compound IIIA) is obtainable according to Coll. Czech. Chem. Commun., 1973, 38, 1159.

We claim:

1. A process for the preparation of the substantially geometrically and optically pure trans-stereoisomeric form of a compound of the formula:

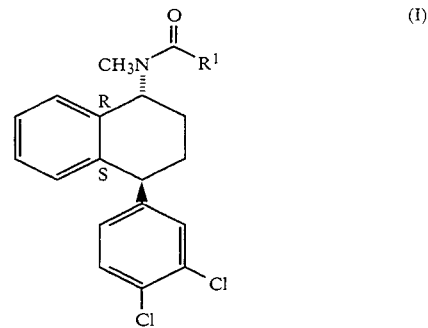

wherein R¹ is H or C₁–C₄ alkyl, and R and S represent the absolute configurations of the asymmetric centres, which comprises ionic hydrogenation of a compound of the formula:

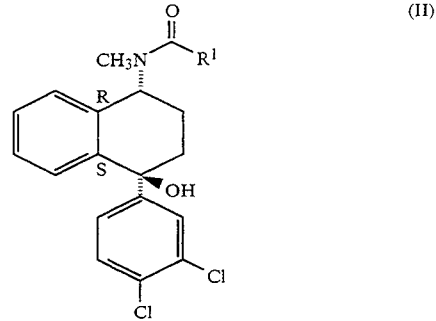

wherein R¹ R and S are as defined for formula (I) .

2. A process as claimed in claim 1 wherein the ionic hydrogenation is achieved using a Lewis acid in conjunction with a hydride donor.

3. A process as claimed in claim 1 wherein the ionic hydrogenation is achieved using a protic acid in conjunction with a hydride donor.

4. A process as claimed in claim 2 wherein the Lewis acid is boron trifluoride.

5. A process as claimed in claim 3 wherein the protic acid is trifluoroacetic acid.

6. A process as claimed in claim 2 wherein the hydride donor is triethylsilane.

7. The substantially geometrically and optically pure trans-stereoisomeric form of a compound of the formula:

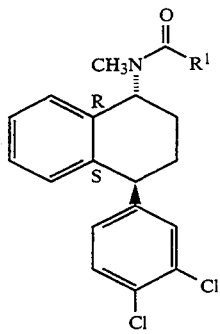

(I)

wherein $R^1$ is H or $C_1$–$C_4$ alkyl, and R and S represent the absolute configurations of the asymmetric centres.

8. A process as claimed in claim 1 wherein $R^1$ is hydrogen.

9. A process as claimed in claim 3 wherein the hydride donor is triethylsilane.

10. A compound as claimed in claim 7 wherein $R^1$ is H.

11. A compound of the formula:

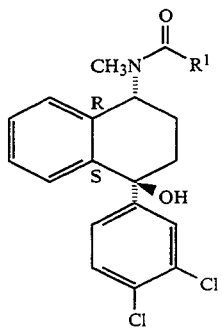

(II)

wherein $R^1$ is H or $C_1$–$C_4$ alkyl, and R and S represent the absolute configurations of the asymmetric centres.

12. A compound as claimed in claim 11 wherein $R^1$ is H.

* * * * *